(12) United States Patent
Chen et al.

(10) Patent No.: US 8,193,217 B2
(45) Date of Patent: Jun. 5, 2012

(54) POLYMORPHIC FORM OF GRANISETRON HYDROCHLORIDE AND METHODS OF MAKING THE SAME

(75) Inventors: Shu-Ping Chen, Kaohsiung (TW); Hsiao-Ping Fang, Yongkang (TW)

(73) Assignee: ScinoPharm Taiwan Ltd., Tainan County (TW)

( * ) Notice: Subject to any disclaimer, the term of this patent is extended or adjusted under 35 U.S.C. 154(b) by 423 days.

(21) Appl. No.: 12/542,968

(22) Filed: Aug. 18, 2009

(65) Prior Publication Data

US 2010/0048613 A1 Feb. 25, 2010

Related U.S. Application Data

(60) Provisional application No. 61/189,421, filed on Aug. 19, 2008.

(51) Int. Cl.
*A61K 31/439* (2006.01)
*C07D 401/12* (2006.01)
*A61P 43/00* (2006.01)

(52) U.S. Cl. ......................... 514/304; 546/126
(58) Field of Classification Search ................... 514/304; 546/126

See application file for complete search history.

(56) References Cited

U.S. PATENT DOCUMENTS

2005/0191349 A1 9/2005 Boehm et al.
2006/0183901 A1 8/2006 Fatheree et al.

FOREIGN PATENT DOCUMENTS

| CN | 101445506 | | 3/2009 |
| WO | 2007088557 | * | 8/2007 |
| WO | WO 2007/088557 | | 8/2007 |
| WO | 2008117282 | * | 10/2008 |
| WO | 2008151677 | * | 12/2008 |

* cited by examiner

*Primary Examiner* — Niloofar Rahmani

(57) ABSTRACT

Crystalline granisetron hydrochloride characterized by a powder x-ray diffraction pattern with peaks at about 14.3, 20.4, and 23.0±0.2 degrees two-theta and process of making the same are disclosed.

16 Claims, 3 Drawing Sheets

Peaks:

| Position (Deg.) | (DSp.) | ESD (Deg.) | Corr.Fact | Intensity (cps) | Rel. Int. (%) | FWHM (L) | ESD (Deg.) | Area | Source Curve | Strain | CSize | CSize Source |
|---|---|---|---|---|---|---|---|---|---|---|---|---|
| 9.8856 | 8.9400 | 0.0000 | 0.0000 | 553.53 | 19.39 | 0.1200 | 0.0000 | 88.6 | PFind None | 0.00 | 0.00 | None |
| 10.1538 | 8.7045 | 0.0000 | 0.0000 | 658.52 | 23.06 | 0.1600 | 0.0000 | 92.2 | PFind None | 0.00 | 0.00 | None |
| 13.2669 | 6.6681 | 0.0000 | 0.0000 | 269.35 | 9.43 | 0.1200 | 0.0000 | 43.1 | PFind None | 0.00 | 0.00 | None |
| 14.2906 | 6.1927 | 0.0000 | 0.0000 | 2855.43 | 100.00 | 0.1600 | 0.0000 | 399.8 | PFind None | 0.00 | 0.00 | None |
| 14.8969 | 5.9420 | 0.0000 | 0.0000 | 330.25 | 11.57 | 0.1400 | 0.0000 | 33.0 | PFind None | 0.00 | 0.00 | None |
| 15.2906 | 5.7898 | 0.0000 | 0.0000 | 675.95 | 23.67 | 0.1600 | 0.0000 | 108.2 | PFind None | 0.00 | 0.00 | None |
| 16.9731 | 5.2195 | 0.0000 | 0.0000 | 932.30 | 32.65 | 0.1200 | 0.0000 | 111.9 | PFind None | 0.00 | 0.00 | None |
| 17.5050 | 5.0621 | 0.0000 | 0.0000 | 1183.23 | 41.44 | 0.1600 | 0.0000 | 189.3 | PFind None | 0.00 | 0.00 | None |
| 18.2244 | 4.8639 | 0.0000 | 0.0000 | 1464.02 | 51.27 | 0.1200 | 0.0000 | 234.2 | PFind None | 0.00 | 0.00 | None |
| 19.2506 | 4.6068 | 0.0000 | 0.0000 | 482.95 | 16.91 | 0.1600 | 0.0000 | 58.0 | PFind None | 0.00 | 0.00 | None |
| 19.8162 | 4.4766 | 0.0000 | 0.0000 | 318.23 | 11.14 | 0.1200 | 0.0000 | 38.2 | PFind None | 0.00 | 0.00 | None |
| 20.4450 | 4.3403 | 0.0000 | 0.0000 | 1834.63 | 64.25 | 0.1400 | 0.0000 | 293.5 | PFind None | 0.00 | 0.00 | None |
| 21.1000 | 4.2070 | 0.0000 | 0.0000 | 355.00 | 12.43 | 0.1600 | 0.0000 | 35.5 | PFind None | 0.00 | 0.00 | None |
| 21.4600 | 4.1373 | 0.0000 | 0.0000 | 722.87 | 25.32 | 0.1600 | 0.0000 | 115.7 | PFind None | 0.00 | 0.00 | None |
| 22.2519 | 3.9918 | 0.0000 | 0.0000 | 1355.45 | 47.47 | 0.1600 | 0.0000 | 216.9 | PFind None | 0.00 | 0.00 | None |
| 22.9494 | 3.8720 | 0.0000 | 0.0000 | 2019.28 | 70.72 | 0.1400 | 0.0000 | 323.1 | PFind None | 0.00 | 0.00 | None |
| 23.0938 | 3.8481 | 0.0000 | 0.0000 | 1846.32 | 64.66 | 0.1600 | 0.0000 | 295.4 | PFind None | 0.00 | 0.00 | None |
| 25.6419 | 3.4712 | 0.0000 | 0.0000 | 1156.35 | 40.50 | 0.1200 | 0.0000 | 138.8 | PFind None | 0.00 | 0.00 | None |
| 26.0419 | 3.4188 | 0.0000 | 0.0000 | 576.63 | 20.19 | 0.1600 | 0.0000 | 92.3 | PFind None | 0.00 | 0.00 | None |
| 26.7687 | 3.3276 | 0.0000 | 0.0000 | 1695.62 | 59.38 | 0.1600 | 0.0000 | 271.3 | PFind None | 0.00 | 0.00 | None |
| 27.4869 | 3.2423 | 0.0000 | 0.0000 | 1785.85 | 62.54 | 0.1600 | 0.0000 | 285.7 | PFind None | 0.00 | 0.00 | None |
| 28.3969 | 3.1404 | 0.0000 | 0.0000 | 289.97 | 10.15 | 0.1000 | 0.0000 | 40.6 | PFind None | 0.00 | 0.00 | None |
| 28.7800 | 3.0995 | 0.0000 | 0.0000 | 819.17 | 28.69 | 0.1600 | 0.0000 | 131.1 | PFind None | 0.00 | 0.00 | None |
| 29.0869 | 3.0675 | 0.0000 | 0.0000 | 297.75 | 10.43 | 0.1200 | 0.0000 | 35.7 | PFind None | 0.00 | 0.00 | None |
| 29.9456 | 2.9814 | 0.0000 | 0.0000 | 260.78 | 9.13 | 0.0800 | 0.0000 | 31.3 | PFind None | 0.00 | 0.00 | None |
| 30.6669 | 2.9129 | 0.0000 | 0.0000 | 275.52 | 9.65 | 0.1600 | 0.0000 | 27.6 | PFind None | 0.00 | 0.00 | None |
| 31.5138 | 2.8365 | 0.0000 | 0.0000 | 744.65 | 26.08 | 0.1400 | 0.0000 | 104.3 | PFind None | 0.00 | 0.00 | None |
| 35.0125 | 2.5607 | 0.0000 | 0.0000 | 289.65 | 10.14 | 0.1000 | 0.0000 | 29.0 | PFind None | 0.00 | 0.00 | None |
| 36.3053 | 2.4724 | 0.0000 | 0.0000 | 304.20 | 10.65 | 0.1600 | 0.0000 | 48.7 | PFind None | 0.00 | 0.00 | None |
| 36.4475 | 2.4631 | 0.0000 | 0.0000 | 339.33 | 11.88 | 0.1200 | 0.0000 | 40.7 | PFind None | 0.00 | 0.00 | None |
| 36.9400 | 2.4314 | 0.0000 | 0.0000 | 278.33 | 9.75 | 0.1000 | 0.0000 | 22.3 | PFind None | 0.00 | 0.00 | None |

Fig. 1(C6)

POLYMORPHIC FORM OF GRANISETRON HYDROCHLORIDE AND METHODS OF MAKING THE SAME

RELATED APPLICATIONS

This application claims priority from U.S. Provisional Patent Application Ser. No. 61/189,421 which was filed on Aug. 19, 2008. The entire content of this application is incorporated herein as reference.

BACKGROUND OF THE INVENTION

1. Field of the Invention

The present application relates to polymorphic form of granisetron hydrochloride and processes of making thereof.

2. Description of the Related Art

Granisetron hydrochloride is an anti-emetic drug, used for treatment or prophylaxis of emesis and post operative nausea and vomiting. Granisetron hydrochloride is marketed as solution for injection as well as tablets. The chemical name of granisetron is N-(endo-9-methyl-9-azabicyclo[3.3.2]non-3-yl)-1-methylindazole-3-carboxamide and it is represented by the following structural formula (I):

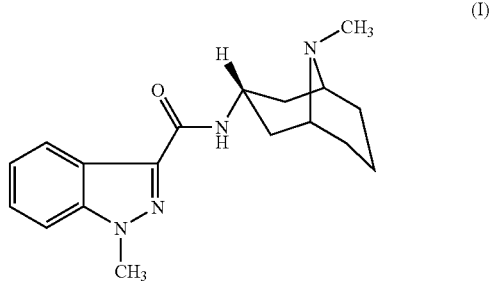

There is a need in the art for a stable, well-defined crystalline granisetron hydrochloride polymorph, which may be conveniently used as the active pharmaceutical ingredient in the preparation of a pharmaceutical composition comprising granisetron hydrochloride, and simple processes for preparing such a polymorph.

SUMMARY OF THE INVENTION

In accordance with one aspect of the present application, a crystalline granisetron hydrochloride form characterized by a powder x-ray diffraction pattern with peaks at about 14.3, 20.4, and 23.0±0.2 degrees two-theta is provided.

Preferably, the crystalline granisetron hydrochloride is further characterized by a powder x-ray diffraction pattern with peaks at about 18.2, 26.8, and 27.5±0.2 degrees two-theta. More preferably, the crystalline granisetron hydrochloride is further characterized by a powder x-ray diffraction pattern with peaks at about 17.5, 22.3, and 25.6±0.2 degrees two-theta. In particular, the crystalline granisetron hydrochloride is further characterized by a powder x-ray diffraction pattern as substantially depicted in FIG. 1a or FIG. 1b.

Preferably, the crystalline granisetron hydrochloride is further characterized by an infrared spectrum having bands at about 3235, 2950, 2450, 1647, and 757 (cm$^{-1}$). More preferably, the crystalline granisetron hydrochloride is further characterized by an infrared spectrum as substantially depicted in FIG. 2.

The crystalline granisetron hydrochloride described above at a therapeutically effective amount may be formulated with at least one pharmaceutically acceptable excipient into a pharmaceutical composition. The pharmaceutical composition may be administered to a patient for treating emesis, post operative nausea, or vomiting.

In accordance with another aspect of the present application, a process of preparing a crystalline granisetron hydrochloride comprises the steps of:

a) combining a crude granisetron hydrochloride in a solvent selected from the group consisting of acetonitrile, tetrahydrofuran, acetone, and combinations thereof to form a mixture of the crude granisetron hydrochloride and the solvent;

b) heating the mixture of a) to an elevated temperature so that the crude granisetron hydrochloride is dissolved in the solvent; and c) cooing the mixture of b) to a lowered temperature so that the crystalline granisetron hydrochloride precipitates.

Preferably, the lowered temperature is lower than 30° C., more preferably, lower than 10° C.

Preferably, the method further comprises a step of adding an anti-solvent to the mixture to facilitate the formation of the crystalline granisetron. The anti-solvent is preferably isopropylether.

In accordance with yet another aspect of the present application, a process of preparing a crystalline granisetron hydrochloride comprises the steps of:

a') combining a crude granisetron hydrochloride with a solvent to form a mixture of the solvent and the crude granisetron hydrochloride;

b') heating the mixture to an elevated temperature so that the crude granisetron is dissolved in the solvent;

c') adding a hydrochloric acid aqueous solution to the mixture of step b');

d') cooling the mixture of step c') so that the crystalline granisetron hydrochloride precipitates Preferably, the solvent is selected from the group consisting of a lower alcohol ($C_1$-$C_4$), water, acetonitrile, tetrahydrofuran, acetone and combinations thereof. More preferably, the solvent is the mixture of water and acetone.

Preferably, the process comprises, prior to the step d'), an additional step of adding acetone to the mixture of the step c').

Compared to those methods reported by others, by using acetone as a solvent to produce crystalline granisetron in accordance with one embodiment of the present invention, the toluene impurities frequently contained in the crude granisetron hydrochloride may be completely or substantially removed. In addition, by using acetone, one may avoid producing undesired impurities such as alkyl chloride, which is formed during the reaction of alkyl alcohol and hydrochloride (for example, ethylchloride from ethanol, isopropylchloride from isopropanol.)

Other objects and features of the present invention will become apparent from the following detailed description considered in conjunction with the accompanying drawings. It is to be understood, however, that the drawings are designed solely for purposes of illustration and not as a definition of the limits of the invention, for which reference should be made to the appended claims. It should be further understood that the drawings are not necessarily drawn to scale and that, unless otherwise indicated, they are merely intended to conceptually illustrate the structures and procedures described herein.

DETAILED DESCRIPTION OF THE PRESENTLY PREFERRED EMBODIMENTS

Examples

Figure 1A:
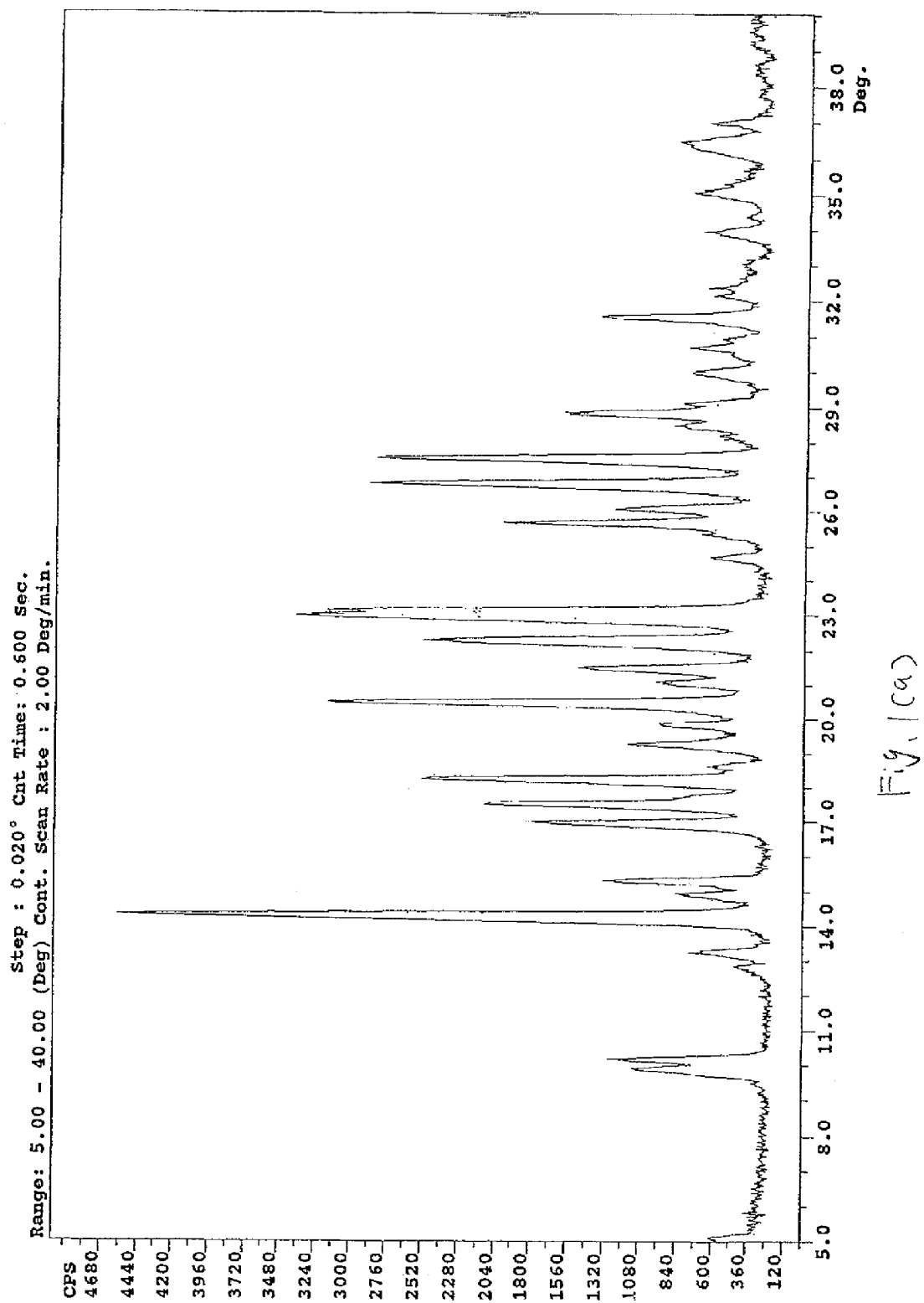
FIG. 1(a-b) depicts the X-ray powder diffraction pattern of crystalline granisetron hydrochloride in accordance with an embodiment of the present invention.

The following examples further illustrate the invention but of course, should not be construed as in any way limiting its scope.

Example 1

Granisetron (60.0 g) and toluene (12 parts) are charged to a suitable reactor and heated to dissolution. Conc. hydrochloric acid (1.1 eq) is added drop wise while maintaining the temperature at 50 to 60° C. The resulting suspension is distilled at below 80° C. to ⅔ volume and cooled to below 10° C. The solid is collected and dried to provide granisetron hydrochloride (53.6-67 g).

Example 2

Granisetron hydrochloride (2 g) and water (about 2.5 parts) are charged to a suitable reactor. The resulting mixture is then heated to dissolve. Acetone (30 parts) is added at about 45° C. The solution is cooled to cloudy, and held for NLT 0.5 h. The slurry is cooled to below 10° C. and held for NLT 1 h, the solids are filtered followed by drying at below 70° C. to provide granisetron hydrochloride (1.62 g, 81% yield).

Example 3

Granisetron hydrochloride (2 g) and 98% n-BuOH aqueous solution (about 30 parts) are charged to a suitable reactor. The resulting mixture is then heated to dissolve. The solution is cooled to cloudy, and held for NLT 2 h. The solids are filtered followed by drying at below 70° C. to provide granisetron hydrochloride (1.52 g, 76% yield).

Example 4

Granisetron hydrochloride (2 g) and 98% n-PrOH aqueous solution (about 32.5 parts) are charged to a suitable reactor. The resulting mixture is then heated to dissolve. The solution is cooled to cloudy, and held for NLT 1 h. The slurry is cooled to below 10° C. and held for NLT 1 h, the solids are filtered followed by drying at below 70° C. to provide granisetron hydrochloride (1.62 g, 81% yield).

Example 5

Granisetron hydrochloride (3 g) and EtOH (about 15 parts) are charged to a suitable reactor. The resulting mixture is then heated to reflux. Water (about 0.03 parts) is added at reflux till dissolution. The solution is cooled to cloudy, and held for NLT 1 h. The slurry is cooled to 20-30° C. and held for NLT 1 h, the solids are filtered followed by drying at below 70° C. to provide granisetron hydrochloride.

Example 6

Granisetron hydrochloride (3 g) and ACN (about 20 parts) are charged to a suitable reactor. The resulting mixture is then heated to reflux. Water (about 1.6 parts) is added at reflux till dissolution. The solution is cooled to cloudy, and held for NLT 1 h. The solids are filtered followed by drying at below 70° C. to provide granisetron hydrochloride.

Example 7

Granisetron hydrochloride (3 g) and THF (about 18 parts) are charged to a suitable reactor. The resulting mixture is then heated to reflux. Water (about 2.3 parts) is added at reflux till dissolution. The solution is cooled to cloudy, and held for NLT 1 h. The solids are filtered followed by drying at below 70° C. to provide granisetron hydrochloride.

Example 8

Granisetron hydrochloride (3 g) and MeOH (about 10 parts) are charged to a suitable reactor. The resulting mixture is then heated to reflux. The solution is cooled to cloudy, and held for NLT 1 h. The slurry is cooled to about 0° C. and held for NLT 1 h, the solids are filtered followed by drying at below 70° C. to provide granisetron hydrochloride.

Example 9

Granisetron hydrochloride (3 g) and MeOH (about 12 parts) are charged to a suitable reactor. The resulting mixture is then heated to dissolve. IPE (about 3 parts) is added at reflux till cloudy and. held for NLT 0.5 h. The slurry is cooled to 20-30° C. and held for NLT 1 h, the solids are filtered followed by drying at below 70° C. to provide granisetron hydrochloride.

Example 10

Granisetron hydrochloride (2 g) and MeOH (about 9 parts) are charged to a suitable reactor. The resulting mixture is then heated to dissolve. Acetone (about 11 parts) is added at reflux. The solution is cooled to 0-10° C. and held for NLT 1 h, the solids are filtered followed by drying at below 70° C. to provide granisetron hydrochloride. (0.86 g, 43% yield)

Example 11

Granisetron hydrochloride (2 g), 5% n-PrOH aqueous solution (about 20 parts) are charged to a suitable reactor. The resulting mixture is then heated to dissolve. The solution is azeotropic drying at reflux under atmosphere and n-PrOH (about 15 parts) was added during distillation. The slurry is then cooled to below 10° C. and held for NLT 1 h, the solids are filtered followed by drying at below 70° C. to provide granisetron hydrochloride (1.8 g, 90% yield).

Example 12

Granisetron hydrochloride (7 g), water (about 1.5 parts) and IPA (about 13.5 parts) are charged to a suitable reactor. The resulting mixture is then heated to dissolve. The solution is azeotropic drying at reflux under atmosphere and IPA (about 15 parts) was added during distillation till cloudy. The slurry is then cooled to below 10° C. and held for NLT 1 h, the solids are filtered followed by drying at below 70° C. to provide granisetron hydrochloride (6.65 g, 95% yield).

Example 13

Granisetron hydrochloride (2 g), water (about 0.75 parts) and absolute EtOH (about 14.25 parts) are charged to a suitable reactor. The resulting mixture is then heated to dissolve. The solution is azeotropic drying at reflux under atmosphere and EtOH (about 20 parts) was added during distillation. The slurry is then cooled to below 10° C. and held for NLT 1 h, the solids are filtered followed by drying at below 70° C. to provide granisetron hydrochloride (1.17 g, 58.5% yield).

Example 14

Granisetron hydrochloride (1.0 Kg, dried basis), water (about 2.0 parts) and acetone (about 5 parts) are charged to a suitable vessel. The resulting mixture is then heated to dissolve. The solution is cooled and 2N HCl solution is added (pH 1-3) at 40 to 50° C. followed by addition of acetone (about 25 parts) at 40 to 50° C. The slurry is then cooled to below 10° C. and held for NLT 1 h, the solids are filtered followed by drying at below 70° C. to provide granisetron hydrochloride (about 0.8 Kg)

The invention is not limited by the embodiments described above which are presented as examples only but can be modified in various ways within the scope of protection defined by the appended patent claims.

We claim:

1. Crystalline granisetron hydrochloride characterized by a powder x-ray diffraction pattern with peaks at about 14.3, 20.4, and 23.0±0.2 degrees two-theta.

2. The crystalline granisetron hydrochloride of claim 1 further characterized by a powder x-ray diffraction pattern with peaks at about 18.2, 26.8, and 27.5±0.2 degrees two-theta.

3. The crystalline granisetron hydrochloride of claim 1 further characterized by a powder x-ray diffraction pattern with peaks at about 17.5, 22.3, and 25.6±0.2 degrees two-theta.

4. The crystalline granisetron hydrochloride of claim 1 characterized by a powder x-ray diffraction pattern as substantially depicted in FIG. 1a or FIG. 1b.

5. The crystalline granisetron hydrochloride of claim 1 further characterized by an infrared spectrum having bands at about 3235, 2950, 2450, 1647 and 757 (cm$^{-1}$).

Figure 2:
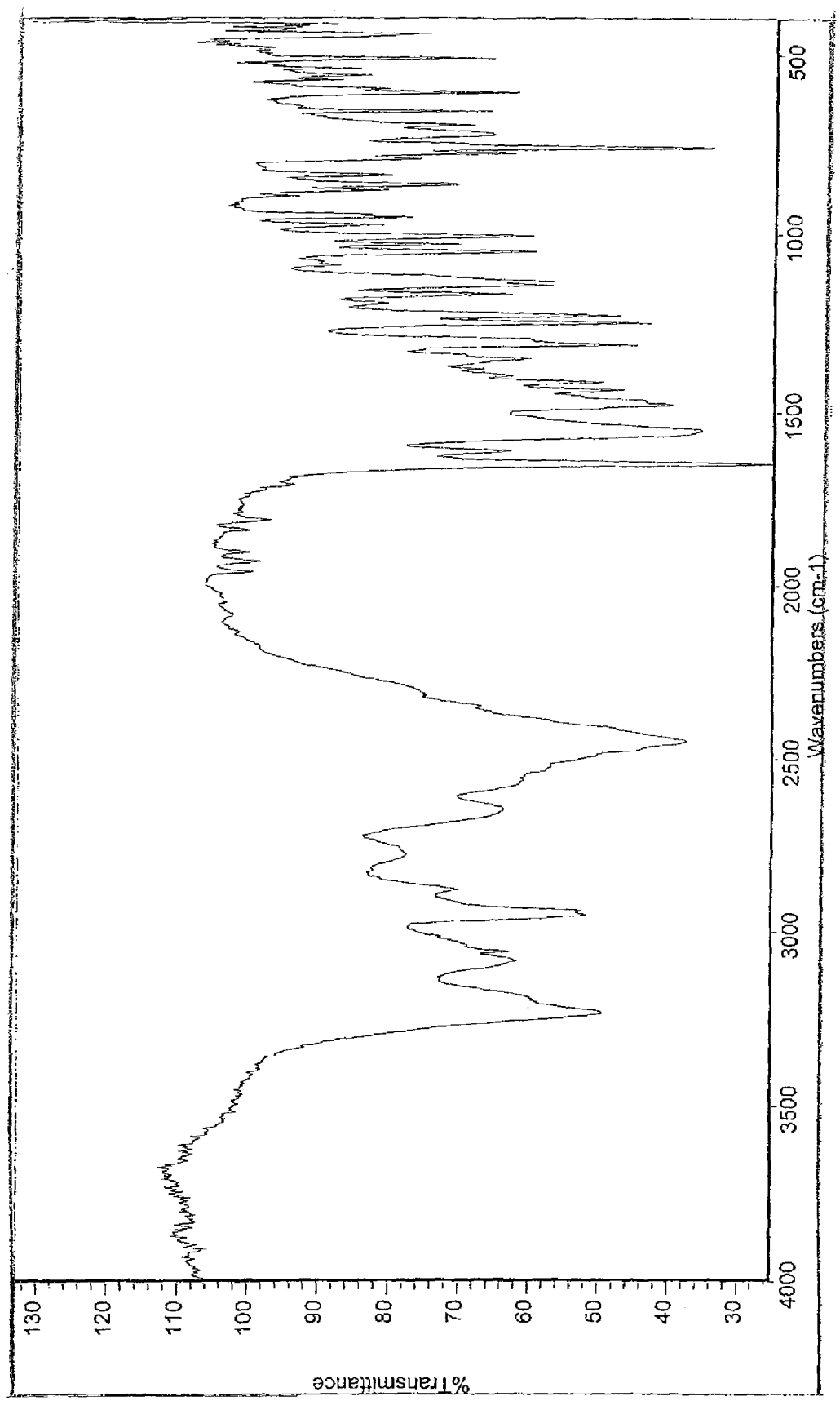
FIG. 2 depicts the infrared spectrum of crystalline granisetron hydrochloride in accordance with an embodiment of the present invention.

6. The crystalline granisetron hydrochloride of claim 1 further characterized by an infrared spectrum as substantially depicted in FIG. 2.

7. A process of preparing a crystalline granisetron hydrochloride of claim 1 comprising the steps of:
   a) combining a crude granisetron hydrochloride in a solvent selected from the group consisting of acetonitrile, tetrahydrofuran, acetone, and combinations thereof to form a mixture of the crude granisetron hydrochloride and the solvent;
   b) heating the mixture of a) to an elevated temperature so that the crude granisetron hydrochloride is dissolved in the solvent; and
   c) cooling the mixture of h) to a lowered temperature so that the crystalline granisetron hydrochloride precipitates.

8. The method of claim 7 wherein the lowered temperature is lower than 30° C.

9. The method of claim 7 wherein the lowered temperature is lower than 10° C.

10. The method of claim 7 further comprising a step of adding an anti-solvent to the mixture to facilitate the formation of the crystalline granisetron.

11. The method of claim 7 wherein the anti-solvent is isopropylether.

12. A process of preparing a crystalline granisetron hydrochloride of claim 1 comprising the steps of:
   a') combining a crude granisetron hydrochloride with a solvent to form a mixture of the solvent and the crude granisetron hydrochloride;
   b') heating the mixture to an elevated temperature so that the crude granisetron is dissolved in the solvent;
   c') adding a hydrochloric acid aqueous solution to the mixture of step be);
   d') cooling the mixture of step c') so that the crystalline granisetron hydrochloride precipitates.

13. The method of claim 12, the solvent is selected from the group consisting of a lower alcohol ($C_1$-$C_4$), water, acetonitrile, tetrahydrofuran, acetone and combinations thereof.

14. The method of claim 12, the solvent is water and acetone mixture.

15. The method of claim 12 wherein the process comprises, prior to the step d'), an additional step of adding acetone to the mixture of the step c').

16. A composition comprising a therapeutically effective amount of the crystalline granisetron hydrochloride of claim 1 and at least one pharmaceutically acceptable excipient.

* * * * *